US009170195B2

(12) United States Patent
Hirning et al.

(10) Patent No.: US 9,170,195 B2
(45) Date of Patent: Oct. 27, 2015

(54) METHOD AND APPARATUS FOR DETERMINING A CURING LEVEL OF PRINTING INKS AND PRINT PROCESS CONTROL STRIP

(75) Inventors: Martin Hirning, Heidelberg (DE); Michael Kohlmann, Frankenthal (DE)

(73) Assignee: Heidelberger Druckmaschinen AG, Heidelberg (DE)

( * ) Notice: Subject to any disclaimer, the term of this patent is extended or adjusted under 35 U.S.C. 154(b) by 577 days.

(21) Appl. No.: 13/349,812

(22) Filed: Jan. 13, 2012

(65) Prior Publication Data

US 2012/0180561 A1    Jul. 19, 2012

(30) Foreign Application Priority Data

Jan. 13, 2011  (DE) .......................... 10 2011 008 489

(51) Int. Cl.
| | |
|---|---|
| G01N 33/32 | (2006.01) |
| G01N 21/55 | (2014.01) |
| G01J 3/46 | (2006.01) |
| G01N 21/35 | (2014.01) |

(52) U.S. Cl.
CPC ................ G01N 21/55 (2013.01); G01N 33/32 (2013.01); *G01J 3/46* (2013.01); *G01N 21/35* (2013.01)

(58) Field of Classification Search
USPC ........... 73/150 R, 341.8; 250/341.8; 118/712; 427/8
See application file for complete search history.

(56) References Cited

U.S. PATENT DOCUMENTS

| | | | |
|---|---|---|---|
| 3,620,727 A * | 11/1971 | Smajo ........................... | 356/404 |
| 5,142,151 A | 8/1992 | Varnell et al. | |
| 5,457,319 A | 10/1995 | Moe et al. | |
| 6,447,836 B1 | 9/2002 | Schrof et al. | |
| 7,262,880 B2 | 8/2007 | Geissler et al. | |

(Continued)

FOREIGN PATENT DOCUMENTS

| | | |
|---|---|---|
| CN | 1541835 A | 11/2004 |
| CN | 101332699 A | 12/2008 |

(Continued)

OTHER PUBLICATIONS

History of Paper, http://www.paperonline.org/history-of-paper, accessed Oct. 4, 2009.*

(Continued)

*Primary Examiner* — Peter Macchiarolo
*Assistant Examiner* — Alexander Mercado
(74) *Attorney, Agent, or Firm* — Laurence A. Greenberg; Werner H. Stemer; Ralph E. Locher

(57) ABSTRACT

A method, apparatus and print process control strip determine a curing level of printing inks on printing material. Conventional measuring areas of a print process control strip are always formed by tonal value combinations of individual, reliably thoroughly dried, printing inks, in particular when using intermediate dryers. Measuring the measuring areas furnishes no more accurate information with regard to the curing level of ink combinations in the actual printed image which differ from the combinations of the measuring areas of the print process control strip. A level-of-curing control area is provided, which is formed by overprinting preferably at least four printing inks, in each case in full tone, to obtain statements relating to the curing level of the printing inks with the print process control strip. Measuring the level-of-curing control area provides information about the curing level of all printing ink combinations in the printed image.

11 Claims, 2 Drawing Sheets

(56) References Cited

U.S. PATENT DOCUMENTS

| | | | |
|---|---|---|---|
| 7,441,443 B2 | 10/2008 | Diedrich et al. | |
| 7,551,317 B2 * | 6/2009 | Engler et al. | 358/1.9 |
| 7,913,622 B2 | 3/2011 | Pitz et al. | |
| 7,954,431 B2 | 6/2011 | Jung et al. | |
| 7,987,717 B2 | 8/2011 | Casagrande et al. | |
| 8,089,667 B2 * | 1/2012 | Gugler et al. | 358/504 |
| 8,520,255 B2 | 8/2013 | Kaiser | |
| 8,807,033 B2 | 8/2014 | Billmaier et al. | |
| 2004/0099806 A1 * | 5/2004 | Shelley et al. | 250/339.01 |
| 2011/0199098 A1 | 8/2011 | Bense et al. | |

FOREIGN PATENT DOCUMENTS

| | | |
|---|---|---|
| CN | 101844438 A | 9/2010 |
| DE | 198 34 184 A1 | 2/2000 |
| DE | 10 2004 053 734 A1 | 5/2006 |
| DE | 10 2006 041 721 A1 | 12/2007 |
| DE | 10 2007 030 566 A1 | 10/2008 |
| DE | 10 2008 041 052 B4 | 4/2010 |
| EP | 0 025 878 A1 | 4/1981 |
| WO | 2004048946 A1 | 6/2004 |

OTHER PUBLICATIONS

Printingforless.com, "How 4 Color Processing (C-M-Y-K) Works", http://www.printingforless.com/processprinting.html, Accessed Dec. 16, 2009.*

Kelsall, Andrew, "The Professional Designer's Guide to using Black", http://www.andrewkelsall.com/the-professional-designers-guide-to-using-black/, Accessed Aug. 13, 2009.*

* cited by examiner

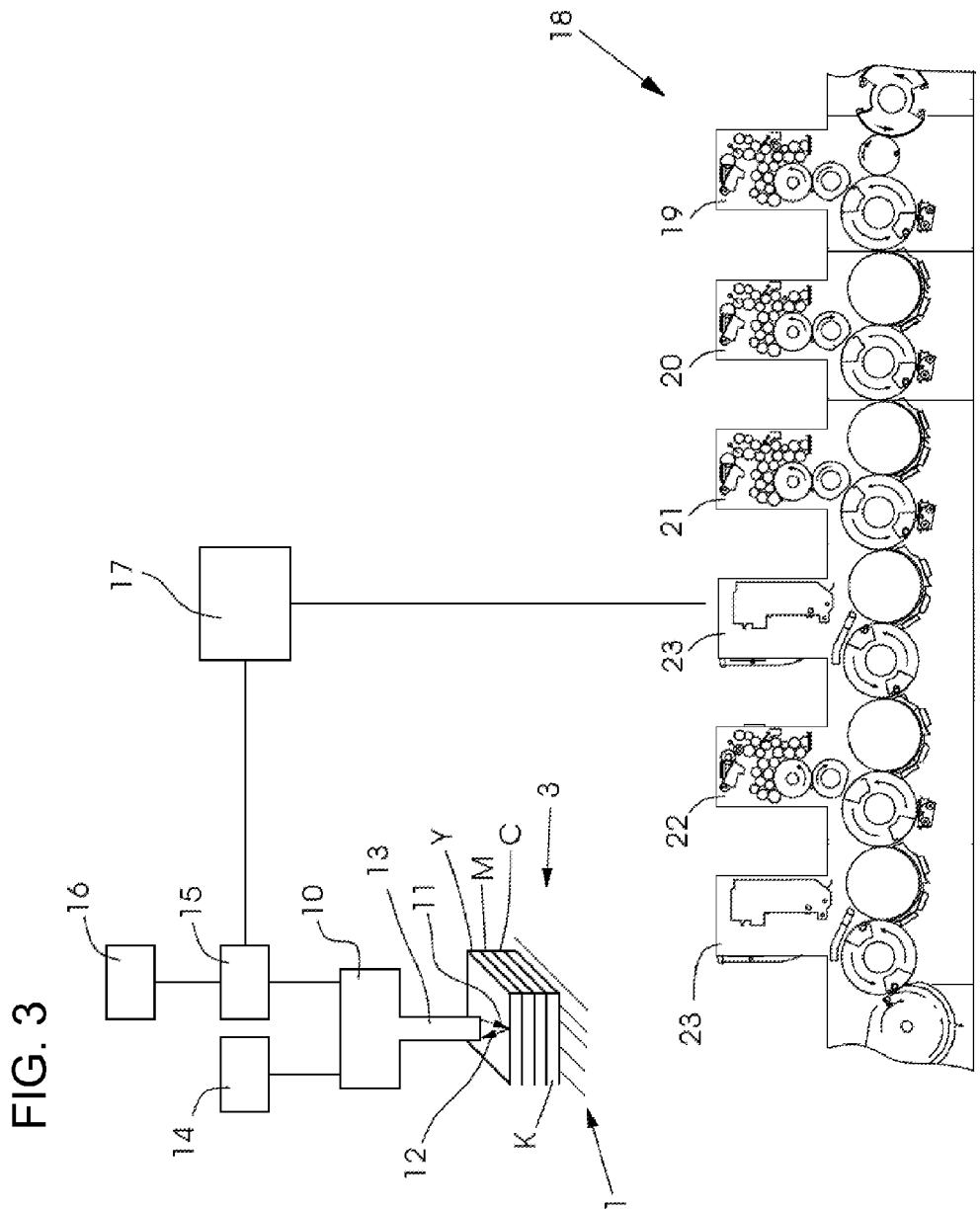

METHOD AND APPARATUS FOR DETERMINING A CURING LEVEL OF PRINTING INKS AND PRINT PROCESS CONTROL STRIP

CROSS-REFERENCE TO RELATED APPLICATION

This application claims the priority, under 35 U.S.C. §119, of German Patent Application DE 10 2011 008 489.4, filed Jan. 13, 2011; the prior application is herewith incorporated by reference in its entirety.

BACKGROUND OF THE INVENTION

Field of the Invention

The invention relates to a method and an apparatus for determining a level of curing of printing inks and/or varnishes on a printing material. Color separations for at least four printing inks and/or varnishes are initially produced in accordance with a printing original and, in accordance with the color separations which are provided, the appropriate printing inks or varnishes are transferred to the printing material in printing and/or varnishing units. In particular, a printing press which is provided for this purpose has the appropriate printing and/or varnishing units for printing the printing material with at least four printing inks or varnishes. In addition to a desired printed image, the color separations have at least one control area and, through the use of a measuring instrument, the level of curing of the printing inks is determined in at least one position in the printed image.

In known printing processes, such as offset, flexographic or gravure printing processes, as well as in industrial inkjet printing processes, it is frequently necessary for printing inks and/or varnish layers which are printed on to be dried or thoroughly cured. That applies, in particular, when using UV inks or UV varnishes. In that case, curing or drying is understood, in particular, to mean the polymerization of the UV inks or varnishes. Appropriate polymerization, i.e. thorough curing and/or drying of the printing inks and/or varnishes, is usually achieved through the use of UV dryers, which are disposed in line in the printing press. When other printing inks and/or varnishes are used, drying differing therefrom, for example through the use of infrared dryers, can also be provided.

Corresponding printing processes for printing the printing material, preferably through the use of UV varnishes or inks, can be used in sheet-fed printing presses or in web-fed printing presses. A precondition for high-quality prints in each case is adequate drying or curing of the printed printing inks and/or varnishes. That is true, in particular, when the inks and/or varnishes have been at least partly overprinted. Incompletely dried or cured printing inks or varnishes can be associated with smearing or blocking of the printed webs or sheets, in particular when they are stacked above one another in the delivery. In that way, firstly the quality of the printed image itself is at least reduced and further processing of the printed product can at least be made more difficult or impossible.

In order to permit the best possible printing quality and the smoothest further processing of the printed products, provision is therefore often made to determine or to monitor the level of drying or curing of the printing inks and/or varnishes. In the following text, in each case mention will be made of the level of curing of the printing inks and/or varnishes. In this case, depending on the type of ink or varnish being used, the level of drying is also intended to be covered.

In order to determine the respective level of curing of the inks or varnishes it is known, for example from German Published Patent Application DE 10 2007 030 566 A1, corresponding to U.S. Pat. No. 7,987,717 and U.S. Patent Application Publication No. US 2008/0240762, to determine the level of drying or level of curing by producing surface waves and measuring the energy density of those waves on the printing material.

European Patent Application EP 0 025 878 A1, corresponding to U.S. Pat. No. 4,469,026, discloses determining the level of curing, at least locally, through the use of an ink density measurement.

Moreover, German Published Patent Application DE 10 2006 041 721 A1, corresponding to U.S. Pat. No. 7,954,431, discloses determining the level of drying globally by measuring the moisture loading of the feed air and the waste air of the dryer device.

The methods and apparatuses known from the prior art normally do not permit the level of drying to be detected finally in each case for all of the combinations of printing inks which are produced one above another in the printed image, in such a way that it is possible to draw conclusions about complete thorough drying of all of the printing inks which have been printed on the printing material. In each case, complicated measurements of global parameters are involved, which do not permit any statement to be made about specific local states, or complicated measurements of local parameters are involved which, once more, do not permit any statement to be made about the global state of all of the locally printed printing ink combinations.

SUMMARY OF THE INVENTION

It is accordingly an object of the invention to provide a method and an apparatus for determining a curing level of printing inks and a print process control strip, which overcome the hereinafore-mentioned disadvantages of the heretofore-known methods, apparatuses and process control strips of this general type and which provide a simpler method and a simpler apparatus for obtaining an at least more reliable statement about the level of drying or the level of curing of printing inks and varnishes.

With the foregoing and other objects in view there is provided, in accordance with the invention, a method for determining a level of curing of printing inks and/or varnishes on a printing material. The method comprises initially producing color separations for four printing inks and/or varnishes in accordance with a printing original, transferring the printing inks and/or the varnishes to the printing material in printing and/or varnishing units, in accordance with the color separations, producing at least one level-of-curing control area by overprinting printing inks and/or varnishes on the printing material, including the at least one level-of-curing control area in addition to a desired printed image in the color separations, and determining the level of curing of the printing inks and/or varnishes at least at one position in the printed image by measuring the at least one level-of-curing control area following printing on the printing material using a measuring instrument while taking the level of curing of the printing ink and/or varnish, preferably a lowest printing ink or a lowest varnish layer, into account.

In the method according to the invention, provision is made for the at least one control area to be a level-of-curing control area. Through the use of a specific level-of-curing control area, it is now sufficient for only this one level-of-curing control area to be measured by a suitable measuring instrument and, merely as a result of determining the level of curing of this level-of-curing control area or through the use of the measured values from the measuring instrument on this level-of-curing control area, to determine whether or not the level of curing of the entire printed image is sufficient for a desired state, or to determine what level of curing has been reached. To this end, provision is made in particular for the level-of-curing control area to be produced by overprinting printing inks and/or varnishes on the printing material. The level of curing of the printing inks and/or varnishes is then determined by measuring the level-of-curing control area by using the measuring instrument following the printing on the printing material. During the determination of the level of curing, in particular the level of curing of at least one of the printing inks being used or one of the varnishes being used is determined, preferably the lowest printing ink or the lowest varnish layer. Since the order of the printing inks and varnishes on the printing material is predefined by the configuration of the printing units within the sheet processing machine, a level of curing of the printing inks and/or varnishes on the printing material is thus preferably determined by determining the level of curing of the ink or varnish layer printed first.

On one hand, a level of curing of the printing ink being measured or of the varnish being measured can be determined. This level of curing provides information overall about the level of curing of the printing inks and varnishes being used, in particular precisely when the printing ink being measured or the varnish being measured is the lowest ink layer. This is advantageously the case precisely when an interdeck dryer is provided within the sheet processing machine, for example a sheet-fed printing press in offset operation, after the first three printing inks, for example the printing inks KCM, i.e. black, cyan and magenta. If these three printing inks are overprinted, then the level of curing of the lowest printing ink provides good information as to the level of curing of all of the printing inks. Of course, printing inks differing from these can also be printed and measured, in particular spot colors.

With the objects of the invention in view, there is also provided an apparatus for determining a level of curing of printing inks and/or varnishes on a printing material. The apparatus comprises a printing press equipped with printing and/or varnishing units in order to print a printing material with at least four printing inks and/or varnishes. The apparatus is intended to have a printing material with the level-of-curing control area described above and, moreover, the apparatus is intended to have a measuring instrument for determining a level of curing of the level-of-curing control area. As described above, this measuring instrument is preferably intended to determine the level of curing of at least one of the printing inks or varnishes being used, preferably the printing ink printed first or the varnish printed first.

With the objects of the invention in view, there is furthermore provided a print process control strip, comprising at least one control area for use in the method or the apparatus according to the invention, the control area being a level-of-curing control area for determining a level of curing of printing inks and/or varnishes on the printing material. In particular, an individual control area, which is the defined level-of-curing control area, is also to be understood as a complete print process control strip in the sense of this invention. Otherwise, it is entirely possible to imagine that the level-of-curing control area according to the invention is integrated as a further measuring area in a conventional print process control strip which has different measuring areas with overprinted printing inks of different tonal values.

With the objects of the invention in view, there is additionally provided a print process control strip provided in a computer program product which is stored on a data storage medium.

With the objects of the invention in view, there is also provided a print process control strip, comprising the level-of-curing control area which is provided on a printing plate or another intermediate carrier for a printed image. Therefore, with the objects of the invention in view, there is also provided a corresponding intermediate carrier. The same is also true of a print process control strip which is provided on a printed end product or on a printed printing material, for example a sheet of paper.

According to the method of the invention, this print process control strip according to the invention can be printed on a printing material and measured by a measuring instrument. This printing and measuring can be performed by the apparatus according to the invention. Furthermore, provision can be made for a statement relating to the level of curing of the printing inks or varnishes being used to be determined and, on the basis of this level of curing, for at least one parameter of the printing press to be controlled in such a way that an optimal level of curing for improving the quality of the printed product is achieved. The adjustable parameters can, for example, be the intensity or the wavelength of the dryer device or the speed of passage of the printing material through the dryer device. A method modified in this way is no longer exclusively a method for determining a level of curing of printing inks and/or varnishes but is also a method, an apparatus and a print process control strip for controlling the level of curing of the printing inks and varnishes within a printing process.

In accordance with another particularly preferred mode of the method of the invention, the level-of-curing control area is produced in at least four color separations. These at least four color separations then serve as a basis for producing the printed image. In offset printing, these color separations firstly serve to generate printing forms, preferably printing plates, which are then used in the actual printing process to transfer ink to the printing material.

In the printing process itself, at least four printing inks are then overprinted in accordance with the at least four color separations, and in this way the level-of-curing control area is produced on the printing material on the basis of these at least four color separations. In this case, combinations of at least four printing inks and/or varnishes are, of course, also possible. Particularly preferably, individual printing inks or varnishes should be overprinted in such a way that the color values of the individual printing inks or varnishes in each case correspond to a full tone, i.e. a color value of 100%. The level-of-curing control area is then produced in such a way that at least four full-tone printing inks are overprinted. Such a level-of-curing control area produced in this way then corresponds to an ink coverage of at least 400%. In conventional process control strips, overprints of four printing inks are not provided. In particular, no provision is made for three colored printing inks and the printing ink black to be overprinted in full tones. According to the invention, it is precisely this overprinting of at least three printing inks over the printing ink black that has the advantage that the printing ink black then serves as a starting point for complete curing of all of the printing inks of the printed image.

In accordance with a further feature of the invention, the level-of-curing control area is produced at least from the printing inks CMYK, with the color black being transferred to the printing material as the lowest printing ink. By measuring the printing ink black, i.e. by measuring the lowest ink layer, a reliable value can then be determined as to whether or not curing has taken place or which level of curing the printing inks or varnishes have. For this purpose, an appropriate level-of-curing control area is provided within the print process control strip, which is produced from the overprinting of at least four printing inks or varnishes in full tone. When further or other printing inks are used, a printing ink different from black can possibly also be printed right at the bottom.

In accordance with an added feature of the invention, the lowest ink is preferably an ink which dries out slowly, i.e. a slowly drying printing ink or a slowly drying varnish. In particular, it should most advantageously be the slowest drying printing ink in the printing process. In this way, by determining the level of curing of the lowest print or varnish layer, i.e. preferably the black ink, a particularly reliable value relating to the level of curing of all of the inks can be achieved. This is true in particular since, in general, an interdeck dryer is always provided immediately after the first three inks. In conventional print process control strips, the black ink will not be found in combination with three further printing inks in full tone. Such a solid build-up can then for the first time give corresponding information about the level of curing of the printing inks. Known control areas of a print process control strip generally exhibit the overprinting of three colored printing inks, with two printing inks already being transferred to the printing material before the first interdeck dryer, in particular when UV printing inks are used. The level of curing of the individual printing inks is then determined by the action of the dryer on two ink layers, in particular a black ink layer never being dried on its own. In an actual printed image, a combination of different ink layers is frequently also applied to black, in order to obtain information about the level of curing of this combination of printing inks, including the black ink. According to the invention the overprinting of all printing inks including the black ink, in each case in full tone, is now provided in the print process control strip.

In accordance with an additional feature of the invention, a measuring instrument is used in order to determine the level of curing of this level-of-curing control area on the basis of the level-of-curing control area produced in this way. For this purpose, an IR measuring instrument which emits radiation in the infrared range is advantageously provided. The reflected radiation is then measured by the measuring instrument and the ratio between emitted and reflected radiation provides information about the level of curing of the printing inks being used. For this purpose, in order to measure the level of curing, firstly a measuring head of the IR measuring instrument is brought into contact with the level-of-curing control area. In order to produce the contact between measuring head and level-of-curing control area, an appropriate controller is provided. Depending on the intensity of the infrared radiation emitted, the thickness of the printing inks and the level of curing of the printing inks, different ratios between reflected and emitted radiation are determined. The penetration depth of the measuring head should be chosen in such a way that reflection from the printing material itself is not also measured. This ideal penetration depth can be determined through the use of an iterative experimental method, in which different thicknesses of printing inks are applied over one another in order in each case to determine the influence of the printing material on completely thoroughly dried printing ink surfaces in relation to the reflected IR radiation. Due to the use of the appropriately set IR measuring head, which has been brought appropriately into contact with the level-of-curing control area, a statement about the level of curing, i.e. the level of curing of the level-of-curing control area, can then be determined. The measuring method described herein operates on the principle of attenuated total reflection (ATR).

In accordance with yet another feature of the invention, the controller of the IR measuring instrument should be constructed in such a way that the contact pressure is advantageously set such that partial mixing of at least some of the printing inks occurs, at least in a boundary area of the individual ink layers underneath the measuring head. In this way, the curing of different ink layers in the level-of-curing control area can be determined in a straightforward way. However, a better result is always achieved when the inks are dried in such a way that they just do not mix.

In accordance with yet a further feature of the invention, for this purpose, the measuring head of the IR measuring instrument should be set up in such a way that substantially the reflection at/in the lowest printing ink or the lowest varnish layer is used to determine the level of curing. In this case, the measuring instrument should be set up in such a way that, if possible, no reflection occurs at the surface of the printing material. Then, as described, an IR measuring instrument can be set up precisely in such a way that no reflections occur at the surface of the printing material and the lowest printing ink or the lowest varnish layer is used as a basis for determining the level of curing if a previously determined ideal distance of the IR measuring instrument from the printing material surface, i.e. an optimal penetration depth of the measuring head into the printing ink layers, is set. Of course, radiation is also always reflected from the upper ink layers, but it is assumed in this case that, even during curing of the upper layers, the lowest layer might still not have dried out completely. This layer is therefore the most relevant.

In accordance with yet an added feature of the invention, for the appropriate positioning of the measuring head of the IR measuring instrument, in terms of apparatus, a controller is provided which sets the position of the measuring head under control in such a way that at least reflections from the lowest ink or varnish layer are measured without any reflections on the printing material occurring. Furthermore, the controller can alternatively or additionally set the contact pressure of the measuring head on the level-of-curing control area or on the printing ink layers belonging thereto in such a way that mixing of at least some printing inks or varnishes occurs, at least in the boundary areas of the individual layers. Such mixing should then no longer occur in the event of complete drying.

In accordance with a concomitant feature of the invention, in a possible alternative, a non-contact measuring method can also be conceivable. In this case, IR radiation is then emitted appropriately into the ink layers in such a way that reflections from the printing material are always also measured at the same time. These printing material emissions can be determined in a test measurement and calculated out of the measurement when measuring the level-of-curing control area. The measured results obtained in this way will then give information about the level of curing of all of the printing inks and/or varnishes.

Other features which are considered as characteristic for the invention are set forth in the appended claims.

Although the invention is illustrated and described herein as embodied in a method and an apparatus for determining a curing level of printing inks and a print process control strip, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 3 includes a longitudinal-sectional view of a printing press and a block diagram of an apparatus for determining a level of curing of printing inks.

DETAILED DESCRIPTION OF THE INVENTION

Figure 1:
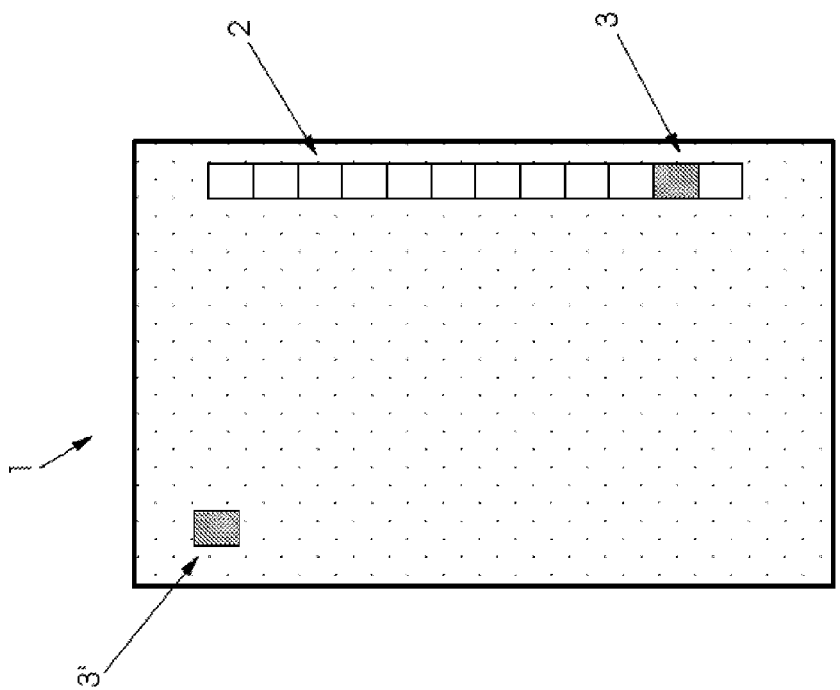
FIG. 1 is a diagrammatic, top-plan view of a printing sheet having level-of-curing control areas.

Referring now to the figures of the drawings in detail and first, particularly, to FIG. 1 thereof, there is seen a printing sheet 1. This sheet 1 is firstly provided with a printed image, which is not explained further herein, as well as with a print process control strip 2. The print process control strip 2 can have different measuring areas, which can ensure printing control and control of the printing process itself. The possible uses of a print process control strip include, for example, determining a tonal value gain. This print process control strip can have a level-of-curing control area 3 according to the invention. Such a level-of-curing control area 3 can also be provided as a separate, independent level-of-curing control area 3' which can be provided on the printing sheet 1 outside of the print process control strips 2 and used further. This individual separate level-of-curing control area 3' can then itself in turn be viewed as a special case of a print process control strip 2.

Figure 2:
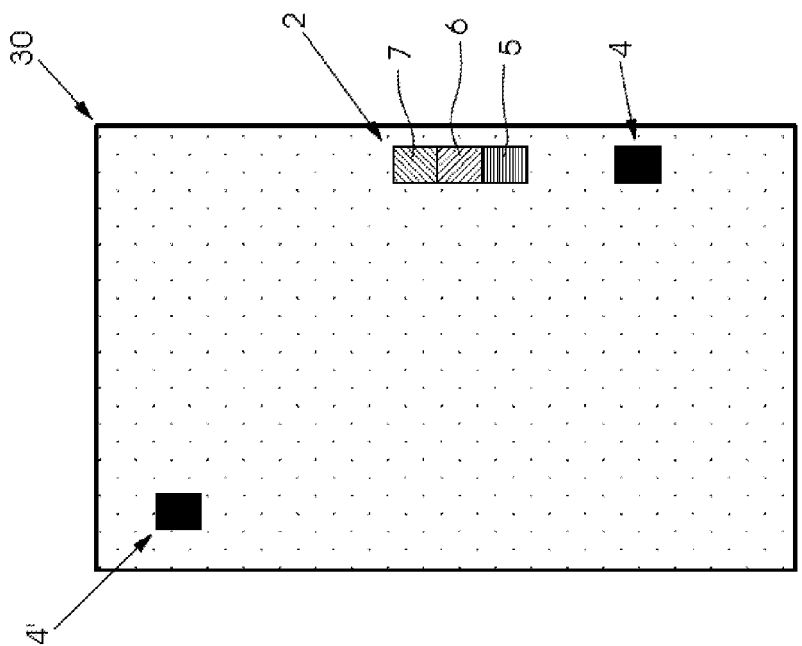
FIG. 2 is a top-plan view of a color separation having level-of-curing control areas.

FIG. 2 shows an individual color separation 30, which is assigned to one of the printing inks being used, e.g. CMYK. For reasons of clarity, the illustration of a printed image possibly to be printed has been dispensed with and only measuring areas 5, 6, 7 of the print process control strip 2, which define different tonal values of the printing ink representing the color separation 30, are shown. These measuring areas 5, 6, 7 having different tonal values of the printing ink being used, belonging to the color separation 30, then result in different measuring areas in the printing sheet 1, for example in the overprint of different printing inks or else for a tonal value wedge of the individual printing ink of the color separation 30 itself. The print process control strip 2 also includes in each case a level-of-curing control area 4 which represents a full tone of the corresponding color separation 30, i.e. a tonal value of 100% of the printing ink used. Additionally or alternatively, the level-of-curing control area 4 in the color separation 30 can also be provided in this case as a separate level-of-curing control area 4' having full-tone coverage of the corresponding printing ink outside the print process control strip 2, with which an independent print process control strip 2 including only this level-of-curing control area 4' is set up.

The level-of-curing control areas 3, 3' which are illustrated in FIG. 1 are formed by overprinting the different printing inks in a printing press 18, as illustrated in FIG. 3. The tonal values with which the printing ink is transferred to the printing material 1 are predefined by the color separations 30, which represent the individual printing inks used within the printing press 18. As shown in FIG. 2, the color separations 30 for the level-of-curing control area 4, 4' in each respective individual printing ink (CMYK) have a full tone in each case, i.e. an ink coverage of 100%. The level-of-curing control areas 3, 3' therefore result from the overprinting of full-tone areas of the individual printing inks CMYK of the printing press 18. A printing press 18, as is conventionally used when using UV inks, is shown in FIG. 3. In this case, printing inks KCM are applied in the order black, cyan and magenta in a first three printing units 19, 20, 21 to a printing sheet 1 led through the printing press 18. These printing inks are dried in a UV dryer 23 following the printing units 19, 20, 21, i.e. the UV inks are polymerized, so that they cure. In a subsequent printing unit 22, the last color yellow (Y) is then transferred to the printing sheet 1 and finally dried once more with a UV dryer 23.

In previous print process control strips and in control areas previously disclosed on a printing sheet 1, firstly individual full-tone areas of the individual printing inks are applied, i.e. areas with 100% coverage of the individual printing inks on their own. Through the use of the UV dryer 23, which follows the third printing unit 21, these 100% areas are always dried with certainty, in particular when a further dryer 23 follows the last printing unit 22.

In known process control strips, the color black (K) is never overprinted with other colors. It is therefore always thoroughly dried as an individual full-tone color. In addition, the color black (K) is generally the most difficult to dry, which is true in particular in the overprint of the individual printing inks. In known process control strips, combinations of the full tones of the individual printing inks CMYK are overprinted. In each case they obtain coverages of 100% when the inks are printed individually, 200% when two full-tone inks combined with one another are overprinted in each case, or a maximum of 300% when the full-tone inks are all overprinted. In this case, combinations with the color black are not taken into account. An application of 400% ink or the like is never provided.

As is shown, in a conventional offset printing process, the color black is the first which is applied and therefore lies under all of the other inks in the overprint. The color black in the overprint is therefore given a dose of radiation for the first time when the colors cyan and magenta are printed over it in the following inking units 20, 21. Therefore, the color black is the color which, firstly, is per se the most difficult to dry and also, as a result of the predefined color sequence KCM, the color which receives the lowest dose of radiation, since the dryer radiation acting on the black ink layer first dries the ink layers lying above, which are printed onto the color black applied in the printing unit 19 in the following printing units 20, 21. If, then, as described, the level-of-curing control area 3, 3' is formed by all of the color separations 30 of the printing inks CMYK in each case having a level-of-curing control area 4, 4' with a tonal value of 100% full tone, then the level-of-curing control area 3, 3' has a color density of 400% full tone, with the lowest ink layer being formed by the printing ink black (K). Measuring such a level-of-curing control area 3, 3', in particular so that the level of curing of the lowest ink layer, i.e. the printing ink (K) printed first in the first printing unit 19, is determined, permits a final assessment as to whether or not all of the printing inks have been dried by the UV dryers 23. If, through the use of a measurement of the lowest (black) layer, it is determined that that layer has been cured completely, then a level of curing for all of the printing inks used in such a way that all of the printing inks have been cured is reliably determined.

FIG. 3 now shows a structure for determining the level of curing of the individual printing inks (CMYK), in particular by determining the level of curing of the lowest ink layer (K) in the level-of-curing control area 3.

In this case, a level-of-curing control area 3 is generally illustrated by overprinted ink layers KCMY. This level-of-curing control area 3 is located on a printing material 1. The level of curing of the lowest ink layer K is now measured through the use of an IR measuring instrument 10. For this purpose, a measuring head 13 of the IR measuring instrument 10 is brought into contact with the level-of-curing control area 3. The measuring head 13 of the IR measuring instrument 10 then emits IR radiation 11. The position of the measuring head 13 in relation to the different ink layers KCMY of the level-of-curing control area 3 is determined in such a way that the IR radiation 11 has a penetration depth into the level-of-curing control area 3 which is sufficient to reach the lowest ink layer K without reflections on the printing sheet 1 occurring. Electromagnetic radiation is then reflected from the individual ink layers on the basis of this penetration depth of the IR radiation 11. This reflected radiation 12 is measured by the measuring head 13 of the IR measuring instrument 10.

In order to achieve appropriate positioning of the measuring head 13 in relation to the ink layers KCMY, the IR measuring instrument 10 is connected to a controller 14, which permits the IR measuring instrument 10 or else the measuring head 13 on its own to be lowered or raised in order to reach an optimal position.

The measuring head 13 can, for example, be a germanium crystal, which penetrates into the ink layers CMYK by a distance of less than 0.6 µm. The contact pressure predefined through the use of the controller 14 can lead to mixing occurring, at least between the lowest ink layer K and the ink layer C located above, if these two layers have not yet cured fully. If such mixing is detected, this always signifies incomplete curing of the ink layers. The appropriate positioning of the germanium crystal, i.e. the measuring head 13, can be determined through the use of a measuring method in which different penetration depths are predefined and different contact pressures are tried out, the IR radiation 11 and the reflected radiation 12 are measured and then, through the use of scanning electron microscope recordings relating to the actual penetration depth, and by evaluating the effective quality of the measurement, information is collected and used to determine values to achieve an optimal contact pressure and optimal positioning of the measuring head 13. The IR measuring instrument 10 can itself be a standard measuring instrument. In this case, although in principle an in-line measurement on the level-of-curing control area 3, 3' is conceivable with appropriate modifications of the measuring method and of the measuring instrument itself, an off-line measurement is preferred, however, using the standard measuring instrument, i.e. the IR measuring instrument, on a separate workbench. An in-line measurement would always preferably be carried out without contact. In order to draw conclusions about the optimal positioning of the measuring head 13, it is possible in particular to utilize the findings relating to the characteristic reflection behavior of the printing material.

The data determined from the IR measuring instrument 10 in this way is passed on to an evaluation device 15. This evaluation device 15 uses the measured values to determine the level of curing at least of the lowest ink layer (K) and draws conclusions as to the level of curing of all of the other ink layers. In particular, by determining a completely cured lowest ink layer K, it is possible to reliably draw conclusions about cured ink layers CMY. This result determined from the evaluation device 15 can then be transmitted onward to an output device 16, e.g. a monitor. Furthermore, this result from the evaluation device 15 can also be transmitted to a control device 17 for the control of a printing press 18. If it is determined in the evaluation device 15 that the level of curing of the lowest ink layer K, and therefore the level of curing of all of the ink layers, does not reliably result in complete curing of all the ink layers on the printing sheet 1, then the control device 17 can adjust the printing press 18 to such an extent that either the passage speed of the printing sheets 1 through the individual UV dryers 23 is reduced and/or the intensity of the individual UV dryers 23 is increased. Through the use of the subsequent further measurement of the level-of-curing control areas 3, 3' through the use of the IR measuring instrument 10, it is then possible to establish whether or not the changes by the control device 17 are crowned with success. In this way, simply by using a level-of-curing control area 3, 3', which is obtained through overprinting all of the printing inks being used, in particular the printing ink black, in particular at the lowest point, in each case in full tone, it is possible to reliably draw conclusions about complete curing of all of the printing inks in the printed image on the printing sheet 1. If this complete curing is not detected, then the printing press 18 can be controlled and modified by the control device 17 to such an extent that complete drying of all of the printing inks is achieved.

The invention claimed is:

1. A method for determining a level of curing of at least one of printing inks or varnishes on a printing material, the method comprising the following steps:
    initially producing color separations for at least four printing inks or varnishes in accordance with a printing original;
    transferring each of the printing inks or each of the varnishes to the printing material in respective printing units or respective varnishing units, in accordance with the color separations;
    producing at least one level-of-curing control area by overprinting at least one of the printing inks or the varnishes on the printing material with at least three remaining printing inks or varnishes of the at least four printing ink or varnishes;
    the color separations including a measuring area in a print process control strip or an individual control area in addition to a printed image, the measuring area or the control area being the at least one level-of-curing control area; and
    determining the level of curing of all of the printing inks or varnishes by measuring the at least one level-of-curing control area following printing on the printing material using a measuring instrument.

2. The method according to claim 1, which further comprises measuring a lowest printing ink or a lowest varnish layer during the step of determining the level of curing with the measuring instrument.

3. The method according to claim 1, which further comprises carrying out the step of producing the at least one level-of-curing control area by overprinting at least one of at least four printing inks or at least one of the at least four varnishes on the printing material, with a color value of the individual printing inks of the at least one level-of-curing control area in the respective color values corresponding to a full tone.

4. The method according to claim 3, which further comprises carrying out the step of producing the at least one level-of-curing control area by overprinting at least Cyan-Magenta-Yellow-Key printing inks and transferring the color Key or black to the printing material as a lowest printing ink.

5. The method according to claim 1, which further comprises:
    using an IR measuring instrument measuring in the infrared range as the measuring instrument;

providing the IR measuring instrument with a measuring head;

bringing the measuring head into contact with the level-of-curing control area using a controller; and determining the level of curing of at least one of the printing inks or at least one of the printing varnishes on a basis of reflected infrared radiation from the IR measuring instrument.

6. The method according to claim 5, which further comprises controlling a contact pressure of the measuring head with the controller to ensure that a penetration depth of infrared radiation of the IR measuring instrument is at least one of sufficient to determine the level of curing of the lowest ink or varnish layer or restricted so that no reflections occur as a result of the printing material itself.

7. An apparatus for determining a level of curing of printing inks or varnishes on a printing material, the apparatus comprising:

a printing press having printing units or varnishing units for printing a printing material with at least four printing inks or at least four printing varnishes and at least one level-of-curing control area, each of the printing units or each of the varnishing units for printing a respective printing ink or respective varnish; and a measuring instrument configured for determining a level of curing of said at least one level-of-curing control area according to the method of claim 1.

8. The apparatus according to claim 7, wherein said at least one level-of-curing control area is formed of at least four printing inks or at least four printing varnishes overprinted in full tone.

9. The apparatus according to claim 7, wherein:

said measuring instrument is an IR measuring instrument measuring reflections in the near infrared range;

said IR measuring instrument has a measuring head; and said measuring head is configured to use at least reflections from a lowest printing ink or varnish layer.

10. The apparatus according to claim 9, wherein said measuring head uses at least the reflections from the lowest printing ink or varnish layer to determine the level of curing without any reflections occurring at a surface of the printing material.

11. The apparatus according to claim 9, which further comprises a controller controlling a position of said measuring head to measure the reflections from the lowest ink or varnish layer without any reflections on the printing material.

* * * * *